United States Patent [19]

Chen

[11] Patent Number: 4,956,754

[45] Date of Patent: Sep. 11, 1990

[54] ULTRAVIOLET LAMP ASSEMBLY

[76] Inventor: Sen-Lung Chen, No. 371, Min-Tsu Road, Tainan, Taiwan

[21] Appl. No.: 486,909

[22] Filed: Mar. 1, 1990

[51] Int. Cl.$^5$ ............................................. F21V 33/00
[52] U.S. Cl. ................................... 362/101; 362/253; 362/256; 210/169
[58] Field of Search ............... 362/96, 101, 255, 256, 362/253; 210/169, 748

[56] References Cited

U.S. PATENT DOCUMENTS

| | | | |
|---|---|---|---|
| 3,821,514 | 6/1974 | Lambo | 362/101 X |
| 3,908,598 | 9/1975 | Jewson | 362/101 X |
| 4,456,512 | 6/1984 | Bieler et al. | 210/748 X |
| 4,600,974 | 7/1986 | Leu et al. | 362/102 |

Primary Examiner—Stephen F. Husar
Assistant Examiner—Peggy A. Neils
Attorney, Agent, or Firm—Morton J. Rosenberg; David I. Klein

[57] ABSTRACT

An ultraviolet lamp assembly for destroying microorganisms in aquarium water includes an elongated ultraviolet lamp, a compartment member wrapped in a helical pattern around and along the length of the lamp, an elongated refelctor tube enveloping the lamp and compartment member with its inner surface abutting against the outer periphery of the compartment member thus defining a helical water flow passage and plug members secured to open ends of the reflector tube. The plug members are formed with inlet and outlet ports respectively communicating ends of the helical passage and exterior of the assembly.

3 Claims, 5 Drawing Sheets

4,956,754

ULTRAVIOLET LAMP ASSEMBLY

BACKGROUND OF THE INVENTION

This invention relates to devices for purifying water in an aquarium, and more particularly to an improved ultraviolet lamp assembly for such device.

A known ultraviolet lamp assembly used in devices for purifying water in aquarium, as shown in FIG. 1, comprises a tubular housing 1 with open ends, two plugs 3 removably secured to the open ends of the housing 1 against fluid pressure and an ultraviolet lamp 2 retained by the plugs 3 in the housing 1 and cooperating therewith to provide an annular fluid flow channel 13 for fluid to be irradiated. An inlet port 11 is formed in an end portion of the housing 1 for connection to a source of fluid under pressure to be irradiated and is directly communicating with the fluid flow channel 13. An outlet port 12 is formed in another end portion of the housing 1 and is also directly communicating with the fluid flow channel 13 for discharging irradiated fluid.

It is found that in such known devices during operation of the lamp, calcium and other colloidal matter tends to coat the lamp envelope or other transparent medium separating the fluid from the lamp, thus building up a scale or other contamination which reduces the intensity of the ultraviolet rays and therefore reduces the effectiveness of the lamp in destroying the microorganisms. Moreover, the water or fluid to be irradiated flowing directly from inlet port 11 to outlet port 12 is too short in distance and too soon in time spending to be fully sterilized. To this end, the inventor has attempted to make an improved ultraviolet lamp assembly to overcome the drawbacks of a known ultraviolet lamp assembly.

OBJECTS OF THE INVENTION

An object of this invention is to provide an ultraviolet lamp assembly which can diminish the disadvantages of a known assembly.

It is another object of this invention to provide an ultraviolet lamp assembly with a construction allowing for conducting a swirling motion to the water passing therethrough to prolong flowing distance and time spending for an effective irradiating treatment.

DETAILED DESCRIPTION OF THE PREFERRED EMBODIMENTS

Figure 1:
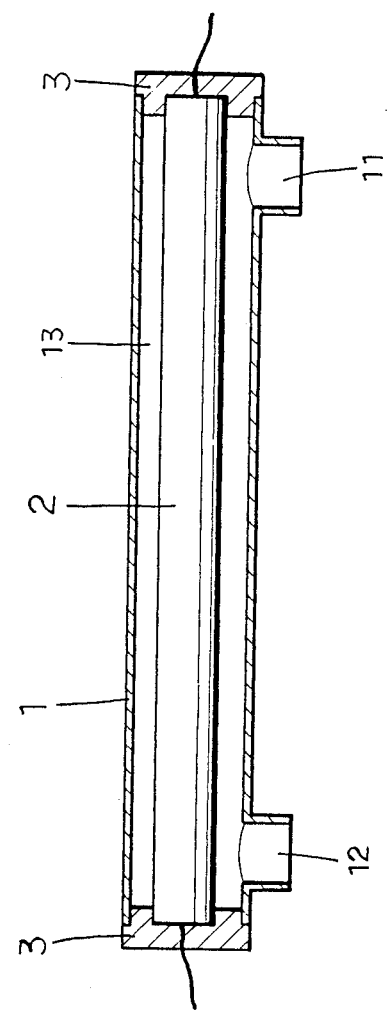
FIG. 1 is a cross-sectional view illustrating a known ultraviolet lamp assembly.
Figure 2:
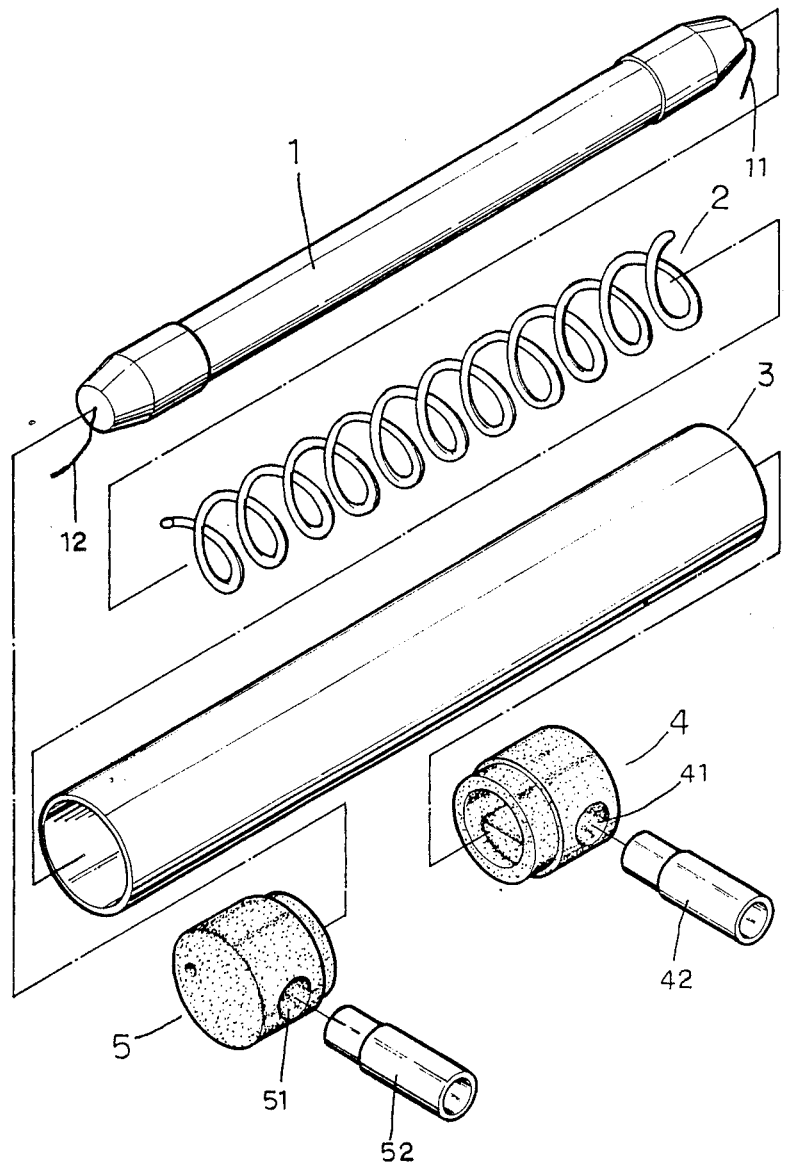
FIG. 2 is an exploded perspective view of the ultraviolet lamp assembly according to this invention.
Figure 3:
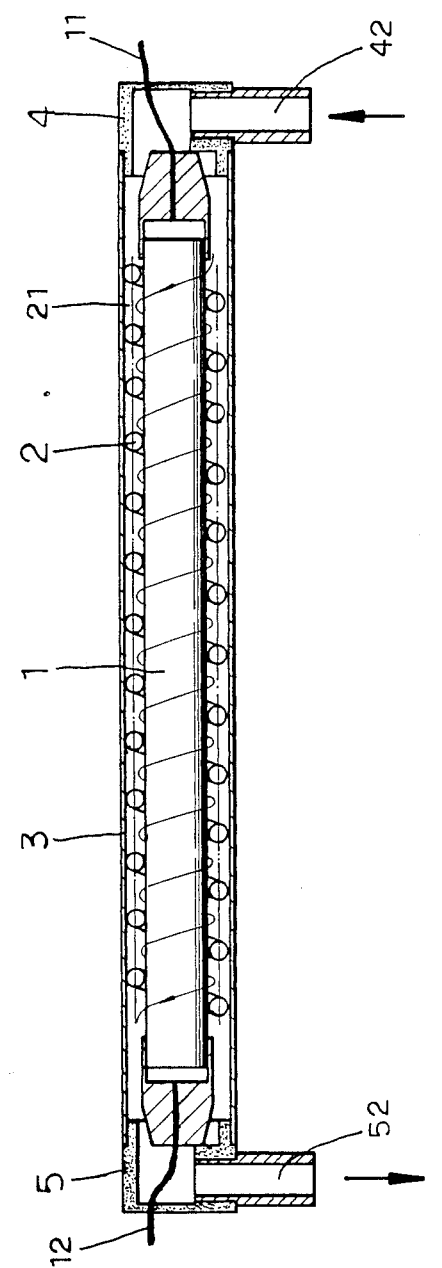
FIG. 3 is a cross-sectional view of this invention which is in assembled state.

Referring to FIGS. 2 & 3, the ultraviolet lamp assembly according to this invention comprises a high intensity ultraviolet lamp 1 and a compartment 2 being wrapped in a helical pattern around and along the length of the lamp 1. The wave length of the ultraviolet lamp 1 is preferably in a range of 1400 to 3900 A and, in general, the effective distance for sterilization of the ultraviolet lamp 1 is 1.0 cm whereby the diameter of cross section of the compartment 2 is preferably 1.0 cm.

A tubular housing 3 of appropriate material and preferably of a material such as stainless steel or other highly reflective material with respective to ultraviolet rays is provided for enveloping the ultraviolet lamp 1 and the helical compartment 3 and has two open ends. Two identical plugs 4, 5 formed with inlet port 41 and outlet port 51 both bent 90 degrees towards attachment ends thereof are secured to the open ends of the housing 3 to seal the same against fluid pressure. The ultraviolet lamp 1 is located in inwardly spaced relation within the reflector housing 3 and extends lengthwise therethrough by means of the helical compartment 2 of which the outer periphery abuts against the inner side wall of the housing 3 and the inner periphery abuts against the outer side wall of the lamp 1 whereby providing a helical fluid flow passage 21 for irradiating water.

The inlet port 41 bent 90 degrees to communicate with the inlet end of the helical passage 21 is press-fitted with an inlet pipe 42 for connection to a water source under pressure to be sterilized in an aquarium and the outlet port 51 bent 90 degrees to communicate with the outlet end of the helical passage 21 is press-fitted with an outlet pipe 52 for discharging irradiated water into the aquarium. The electric supply conductors 11, 12 extend outwardly through the plugs 4, 5.

Said helical passage 21 defined by the compartment 2 between the housing 3 and lamp 1 prolongs the flow distance and time spending of water flow, thus rendering a thorough sterilization to the water to be irradiated. Moreover, the helical passage 21 conducts a swirling motion to the water passing through the assembly to remove any particles which may tend to settle on the lamp covering 1.

Figure 4:
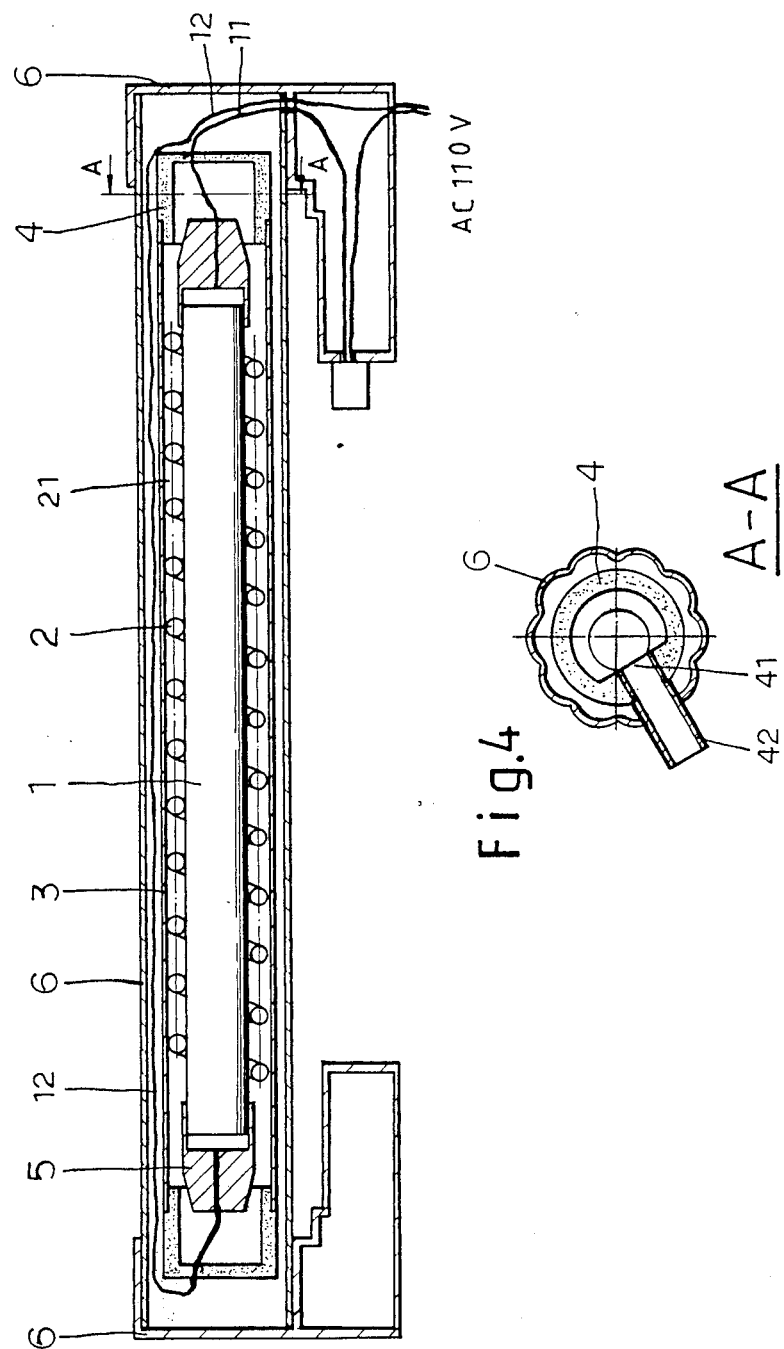
FIG. 4 is a cross-sectional view of the embodiment with a casing ready for installation in an aquarium.

As shown in FIG. 4, the ultraviolet assembly is further provided with a casing 6 for water-tightly enveloping the ultraviolet lamp assembly shown in FIG. 3. Said water inlet pipe 42 is connected to an inlet opening 61 formed in the casing 6 for water suction and said water outlet pipe 52 is connected to an outlet opening 62 formed in the casing 6 for water discharge. Said electric supply conductors 11, 12 are collected at the same side of the assembly and extend outwardly through the casing 6. The ultraviolet assembly so constructed is ready for installation in an aquarium.

Figure 5:
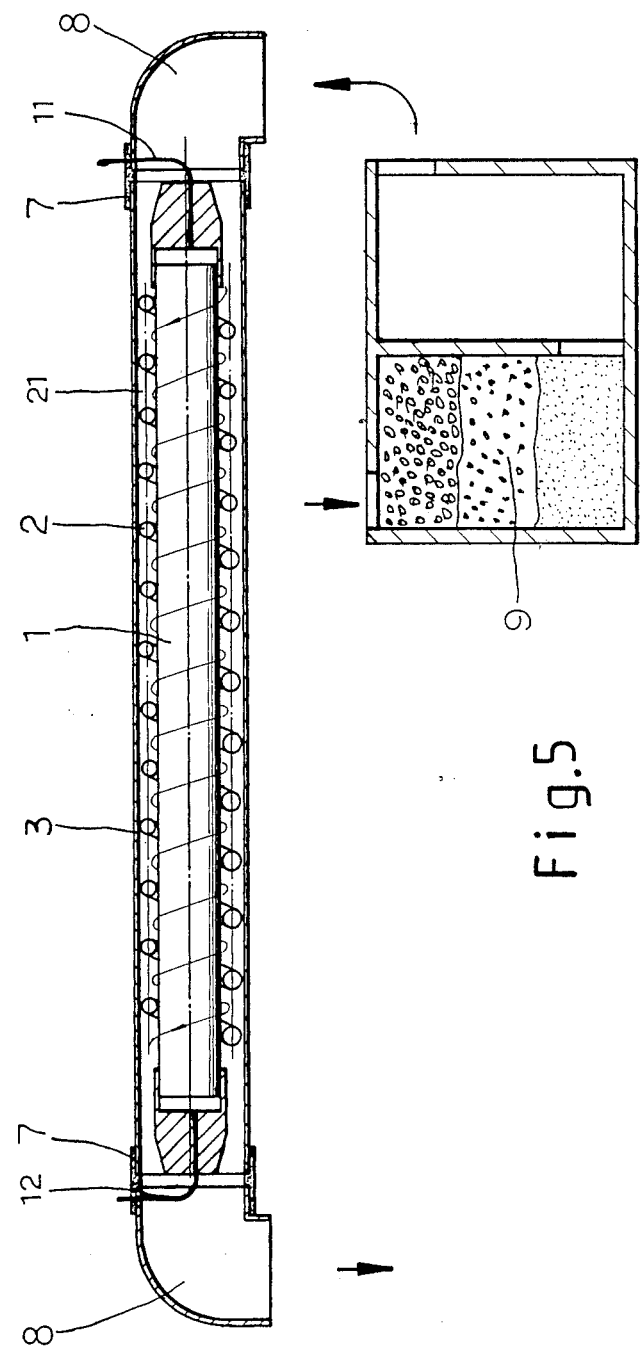
FIG. 5 is a cross-sectional view illustrating another embodiment of this invention.

Referring to FIG. 5, another embodiment of this invention is simplified in construction by providing two identical bends 8 communicatively connected to two open ends of the housing 3 through joints 7. This embodiment of the ultraviolet lamp assembly can be applied to an aquarium in combination with a conventional filter 9 which is accommodated with a loose granular activated charcoal or other suitable filtering material. Water in the aquarium passes first through the filter 9 to filter out any solids and then passes through inlet joint 8 and lengthwise through the helical passage 21 around the ultraviolet lamp assembly where it is thoroughly exposed to ultraviolet irradiation. Finally, the sterilized fluid is discharged through the outlet bend 8.

It is intended that all matter contained in the above description or shown in the accompanying drawing be interpreted as illustrative and not in a limiting sense. It is also to be understood that the following claims are intended to cover all of the generic and specific features of the invention herein described.

What is claimed is:

1. An ultraviolet lamp assembly for immersion in the water of an aquarium comprising:
   an tubular ultraviolet lamp having electric supply conductors;
   a compartment means wrapped in a helical pattern around and along the length of the ultraviolet lamp;
   an elongated reflector means having two open ends and enveloping said ultraviolet lamp and compartment means with its inner surface abutting against an outer periphery of the compartment means for defining a helical fluid flow passage therein;
   plug means secured to the open ends of the reflector means;
   passage means formed in the plug means and communicating ends of the helical passage defined by the compartment means; and
   pipe means connected to the passage means of the plug means for communicating the helical passage and exterior of this assembly.

2. An ultraviolet lamp assembly as claimed in claim 1, wherein the reflector means is made of reflective material with respective to ultraviolet rays.

3. An ultraviolet lamp assembly as claimed in claim 1, wherein the assembly is further encased in a water-tight condition in a casing having openings communicatively connected with the pipe means and the electric supply conductors are collected at one side of the assembly to extend outwardly through the casing.

* * * * *